United States Patent [19]

Lagudah

[11] Patent Number: 5,994,627
[45] Date of Patent: Nov. 30, 1999

[54] GENETIC SEQUENCES CONFERRING NEMATODE RESISTANCE IN PLANTS AND USES THEREFOR

[75] Inventor: Evans Sylvanus Lagudah, Weston, Australia

[73] Assignees: Common Wealth Scientific and Industrial Research Organisation, Campbell; Grains Research and Development Corporation, Barton, both of Australia

[21] Appl. No.: 08/414,938

[22] Filed: Mar. 31, 1995

[51] Int. Cl.⁶ ............ C12N 15/29; C12N 15/82; A01H 4/00; A01H 5/00
[52] U.S. Cl. .......... 800/298; 800/278; 435/69.1; 435/419; 435/468; 435/320.1; 536/23.6; 536/24.1
[58] Field of Search ............ 800/105, DIG. 55, 800/DIG. 56, 295, 278, 298; 435/172.3, 320.1, 69.1, 419, 468; 536/23.6, 24.1

[56] References Cited

U.S. PATENT DOCUMENTS 5,589,622  12/1996  Gurr et al. ............... 800/205

FOREIGN PATENT DOCUMENTS 0 502 730 A1  9/1992  European Pat. Off. ........ C12N 15/82

OTHER PUBLICATIONS

Delibes et al. Theor. Appl. Gentet. vol. 87, pp. 402–408, 1993.
Napoli et al. The Plant Cell. vol. 2, pp. 279–289, Apr. 1990.
Eastwood et al. Aust. J. Agric. Res. vol. 42, pp. 69–77, 1991.
Eastwood, R.F. et al. (1993) "A Directed Search For DNA Sequences Tightly Linked To Cereal Cyst Nematode Resistance Genes In Triticum Tauschii," *Genome* 37: 311–319 (Exhibit 1).
Lagudah, E.S. et al. (1991) "The Molecular–Genetic Analysis Of Triticum Tauschii, The D–Genome Donor To Hexaploid Wheat, " *Genome* 34:375–386 (Exhibit 2).
Slootmaker, L.A.J. et al. (1974) "Monosomic Analysis In Bread Wheat Of Resistance To Cereal Root Eelworm," *Euphytica* 23:497–503 (Exhibit 3).
Williams, K.J. et al. (1994) "Identification Of RFLP Markers Linked To The Cereal Cyst Nematode Resistance Gene (Cre) In Wheat," *Theor. Appl. Genet.* 89:927–930 (Exhibit 4).

*Primary Examiner*—Lynette R. F. Smith
*Assistant Examiner*—Thomas Haas
*Attorney, Agent, or Firm*—John P. White; Cooper & Dunham LLP

[57] ABSTRACT

The present invention relates generally to a nucleic acid molecule encoding, or complementary to a nucleic acid molecule encoding, a polypeptide which confers, enhances, or otherwise facilitates resistance to a nematode in a plant cell. The nucleic acid molecule of the present invention is useful in the isolation of related nematode resistance, or nematode resistance-like genetic sequences, from other plants. Furthermore, the present invention provides for the generation of plants carrying non-endogenous nematode resistance, or nematode resistance-like genetic sequences, said plants exhibiting enhanced tolerance to parasitic nematodes and related pathogens.

27 Claims, 7 Drawing Sheets

DNA from a subset of *T. tauschii* individuals in an F2 population in which *Ccn-D1* is segregating The csE20 sequence is approximately 120 base pairs from the start of transcription of Cre3

R = Resistance    S = Susceptible

- linkage between XcsE20 RFLP marker and *CcnD1* is complete in bread wheat backcross derivatives produced in a program to introduce this gene into commercial cultivars R S S R S S R S R S S S H H S S
parental lines 6.5 kb →

FIG. 6

GENETIC SEQUENCES CONFERRING NEMATODE RESISTANCE IN PLANTS AND USES THEREFOR

FIELD OF THE INVENTION

The present invention relates generally to genetic sequences, and more particulary to genetic sequences which confer, or otherwise facilitate or enhance, resistance in plants to plant parasitic nematodes, such as cyst nematodes and root knot nematodes. The present invention further provides for plants into which the subject genetic sequences have been introduced, generating enhanced resistance qualities to plant parasitic nematodes. The present invention is particularly useful in the development of plants resistant to plant parasitic nematodes such as food, fibre and ornamental plants.

Bibliographic details of the publications referred to by author in this specification are collected at the end of the description. Sequence identity numbers (SEQ ID Nos.) for the nucleotide and amino acid sequences referred to in the specification are defined after the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND TO THE INVENTION

Improvements in recombinant DNA technology have produced dramatic changes to the agricultural industry, in particular the approaches taken to improve crop productivity. A major concern is the effect of plant pests, such as plant parasitic nematodes, on productivity. Generally, plant parasitic nematodes invade a wide range of food, fibre and ornamental plants, causing damage to different plant tissues with varying severity on productivity. Parasitic nematodes cost the agriculture and horticulture industries approximately U.S. $78 billion per annum.

Plant parasitic nematodes are broadly classified as either migratory ectoparasites, sedentary ectoparasites, migratory ectoendoparasites, migratory endoparasites, or sedentary endoparasites, on the basis of their feeding patterns. Most crop damage is caused by sedentary endoparasites, for example the cyst nematodes heterodera sp. and Globodera sp. and the root knot nematodes meloidogyne sp., through their devastating effect on root structures. Juvenile nematodes invade the plant root and migrate to the vascular tissue where they induce a multinucleate feeding structure or syncitium from which the nematode feeds.

The most cost-effective and sustainable method for control of plant pests is the development of resistant plants. However, the development of this method of control in relation to parasitic nematodes has faced many difficulties. For example, bioassays for nematodes, such as the cereal cyst nematode, are long and labour intensive. Although natural resistance to plant parasitic nematodes occures in certain plant genotypes, the molecular basis of resistance was hitherto unknown. In particular, the molecular characteristics of a gene encoding a polypeptide which confers nematode resistance on a plant, has not been a straightforward procedure. Furthermore, until the present invention, even the chromosomal localisation of nematode resistance genes and genetic markers for nematode resistance, were unknown.

SUMMARY OF THE INVENTION

In accordance with the present invention, genetic sequences conferring resistance to a plant pathogen, preferably a plant parasitic nematode, have been cloned from *Triticum tauschii*. The cloning of these sequences permits the generation of transgenic plants with de novo, improved or otherwise enhanced nematode resistance. The present invention also permits the screening through genetic or immunological means, similar nematode resistance genes in other plants for use in developing or enhancing nematode resistance in commercially and economically important species.

Accordingly, one aspect of the present invention provides an isolated nucleic acid molecule comprising a sequence of nucleotides which encodes or is complementary to a nucleic acid molecule which encodes a protein or derivative thereof, which confers, enhances, or otherwise facilitates resistance to a nematode in a plant.

In another embodiment, the present invention provides an isolated DNA molecule comprising a sequence of nucleotides which:

(i) encodes or is complementary to a sequence encoding a polypeptide of plant origin which confers, enhances, or otherwise facilitates nematode resistance in a plant; and (ii) has at least about 40% nucleotide sequence similarity to all or a part thereof the sequence set forth in SEQ ID NO: 1 and/or SEQ ID NO: 3.

In yet another embodiment, the present invention provides an isolated nucleic acid molecule which:

(i) encodes or is complementary to a sequence encoding a polypeptide of plant origin which confers, enhances, or otherwise facilitates nematode resistance in a plant; and (ii) hybridises under at least low stringency conditions to the nucleic acid molecule set forth in SEQ ID NO: 1 and/or SEQ ID NO: 3 or to a complementary strand thereof.

Another aspect of the invention provides a genetic construct comprising a sequence of nucleotides which encodes or is complementary to a nucleic acid molecule which encodes a protein or derivative thereof, which confers, enhances, or otherwise facilitates resistance to a nematode in a plant. According to one embodiment, the nucleic acid molecule is operably linked to a promoter sequence, thereby regulating expression of said nucleic acid molecule in a eukaryotic cell, for example a plant cell, or a prokaryotic cell.

In yet another aspect, the present invention provides a genetic construct comprising an isolated promoter sequence from a gene which when expressed encodes a polypeptide that confers, enhances, or otherwise facilitates nematode resistance in a cell, or a functional part, derivative, fragment, homologue or analogue thereof, operably linked to the coding region isolated from a second genetic sequence.

The present invention also provides an oligonucleotide molecule of at least 10 nucleotides in length capable of hybridising under low stringency conditions to part of the nucleotide sequence, or to a complement of the nucleotide sequence set forth in SEQ ID NO: 1 and/or SEQ ID NO: 3.

The nucleic acid molecule and/or oligonucleotide of the present invention are useful in the isolation of nematode resistance or nematode resistance-like genetic sequences from other plants, using hybridisation and/or PCR-based approaches.

Accordingly, there is provided a method of identifying a nematode resistance genetic sequence or nematode resistance-like genetic sequence which method comprises contacting genomic DNA, or mRNA, or cDNA, or parts, or fragments thereof, or a source thereof, with a hybridisation effective amount of a genetic sequence encoding, or complementary to a genetic sequence encoding a polypeptide which confers, enhances or otherwise facilitates nematode resistance, or a part thereof, and then detecting said hybridisation.

There is also provided a method of identifying a nematode resistance genetic sequence or a nematode resistance-like genetic sequence in a plant cell, which method comprises contacting genomic DNA, mRNA, or cDNA with one or more oligonucleotide molecules to a genetic sequence from said plant for a period of time and under conditions sufficient to form a double-stranded nucleic acid molecule and amplifying copies of the said genetic sequence in a polymerase chain reaction.

In another aspect, this invention also provides an isolated polypeptide which comprises an amino acid sequence which confers, enhances, or otherwise facilitates resistance to a nematode in a plant cell, or a functional mutant, derivative part, fragment, or analogue of said polypeptide.

The present invention extends to a synthetic peptide comprising any part of the amino acid sequence set forth in SEQ ID NO: 2 and/or SEQ ID NO: 4, or having at least 40% similarity to all or a part thereof.

The polypeptide and synthetic peptides of the present invention may be used to generate specific immuno-interactive molecules. Accordingly, the present invention also provides an antibody that binds to a polypeptide comprising an amino acid sequence which:

(i) confers, enhances, or otherwise facilitates resistance to a nematode in a plant; or (ii) is substantially the same as the amino acid sequence set forth in SEQ ID NO: 2 and/or SEQ ID NO: 4, or having at least 40% similarity to all or a part thereof.

In yet another aspect of the present invention, there is provided a method of identifying a nematode resistance gene product or nematode resistance-like gene product in a plant cell, which method comprises contacting the antibody with an antigen from said plant for a period of time and under conditions sufficient to form an antibody-antigen complex and measuring the amount of said antibody-antigen complex formed.

The present invention is useful for the generation of plants with enhanced nematode resistance or nematode resistance-like characteristics and there is also provided a plant carrying a non-endogenous nucleic acid molecule encoding or complementary to a nucleic acid molecule encoding a polypeptide which confers, enhances, or otherwise facilitates nematode resistance in said plant. The present invention extends to the progeny derived from said plant.

BRIEF DESCRIPTION OF THE DRAWINGS

FIG. 6 is a photographic representation showing linkage between the XcsE20 RFLP marker and Cre3 (Ccn-D1) in *Triticum aestivum* resistant (R) and susceptible (S) backcross individuals.

Figure 1:
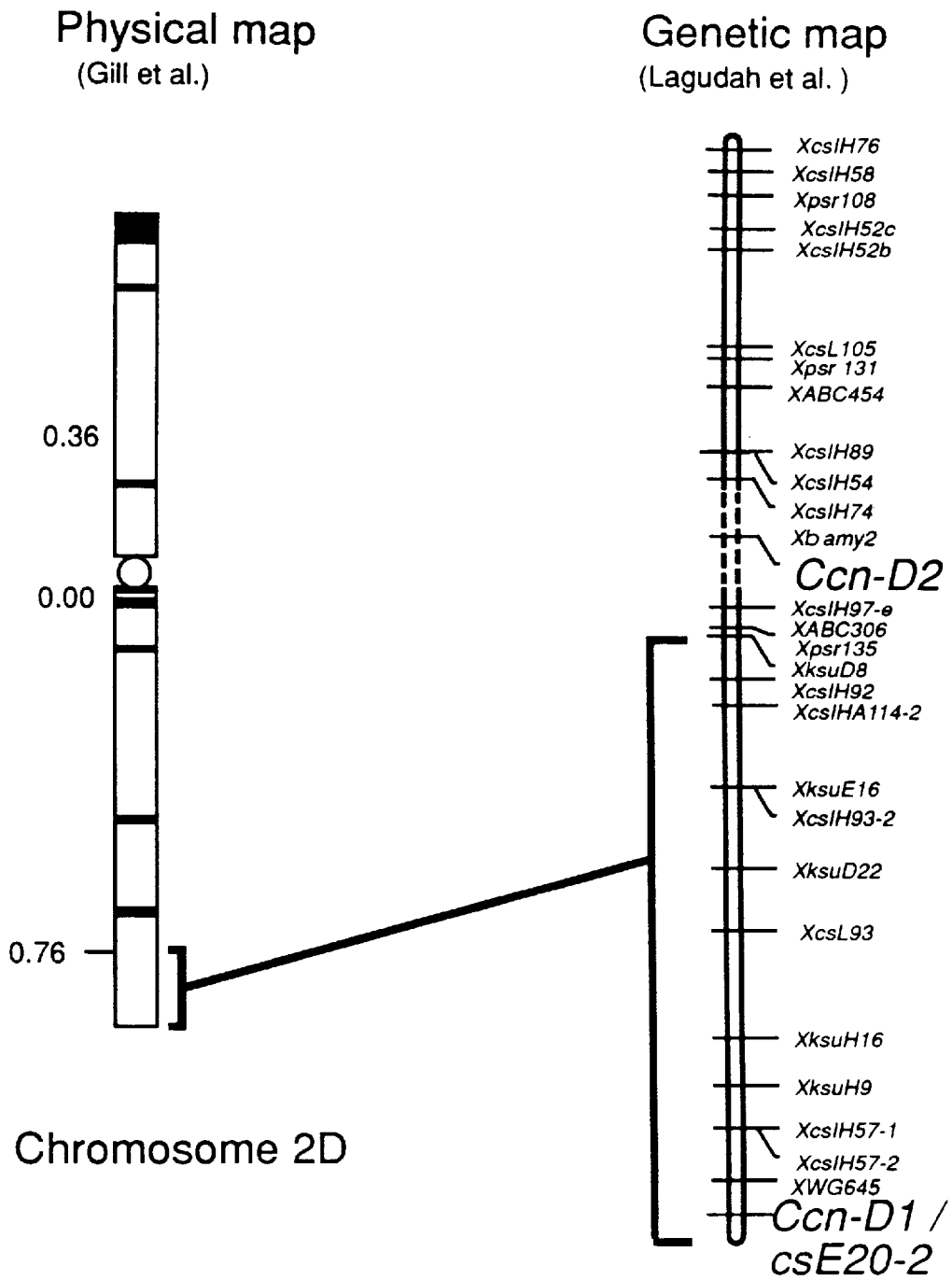
FIG. 1 is a graphical representation of an RFLP linkage and physical map of chromosome 2D produced from *Triticum tauschii* F2 progeny of the genetic crosses (a) CPI 110813×CPI 110795; (b) AUS 18913×CPI 110856. The map location of the nematode resistance genes Ccn-D1 and Ccn-D2 are indicated.

Single letter abbreviations used for amino acid residues in the specification are defined in Table 1.

TABLE 1

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |

TABLE 1-continued

| Amino Acid | Three-letter Abbreviation | One-letter Symbol |
|---|---|---|
| Proline | Pro | P |
| Serine | Ser | S |
| Threonine | Thr | T |
| Tryptophan | Trp | W |
| Tyrosine | Tyr | Y |
| Valine | Val | V |

DETAILED DESCRIPTION OF THE PREFERRED EMBODIMENTS

One aspect of the present invention comprises an isolated nucleic acid molecule comprising a sequence of nucleotides which encodes or is complementary to a sequence which encodes a protein or derivative thereof, which confers, enhances or otherwise facilitates resistance to a nematode in a plant.

Hereinafter the term nematode "resistance gene" or "resistance-like gene", or similar term shall be used to define a nucleic acid molecule which upon expression confers, enhances, or otherwise facilitates resistance of a cell and/or organism to one or more plant parasitic pathogens. The term "nematode resistance gene" further defines a nucleic acid molecule which upon expression confers, enhances, or otherwise facilitates resistance to one or more plant parasitic nematode pathogens. Reference herein to a "gene" is to be taken in its broadest context and includes:

(i) a classical genomic gene consisting of a coding region optionally together with transcriptional and/or translational regulatory sequences and a coding region with or without non-translated sequences (i.e. introns, 5'- and 3'-untranslated sequences);

(ii) mRNA or cDNA corresponding to the coding regions (i.e. exons) and optionally 5'- and 3'-untranslated sequences of the gene.

The term "gene" is also used to describe a synthetic or fusion molecule, or derivative which encodes, or is complementary to a molecule which encodes, all or part of a functional product. A functional product is one which confers, enhances or otherwise facilitates resistance of a cell to a parasitic nematode. Preferred nematode resistance-like genes are derived from a naturally occurring nematode resistance gene by standard recombinant techniques. Generally, a nematode resistance gene may be subjected to mutagenesis to produce single or multiple nucleotide substitutions, deletions and/or additions. Nucleotide insertional derivatives of the nematode resistance gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

The present invention extends to the isolated nucleic acid when integrated into a plant genome and to propagated plants containing same nucleic acid molecule.

Another aspect of the present invention is directed to a nucleic acid molecule which comprises a sequence of nucleotides corresponding or complementary to the nucleotide sequence set forth in SEQ ID NO: 1 and/or SEQ ID NO: 3, or having at least 40% similarity to all or a part thereof and wherein said nucleic acid molecule encodes a protein that confers, enhances, or otherwise facilitates resistance to a nematode in a plant.

Preferably, the percentage similarity to the sequence set forth in SEQ ID NO: 1 and/or SEQ ID NO: 3 is at least 50%. Even more preferably, the percentage similarity is at least 60–65%. Still more preferably, the percentage similarity is at least 70–75%. Yet still more preferably, the percentage similarity as at least 80–90%, including at least 91% or 93% or 95%.

For the purposes of nomenclature, the sequence shown in SEQ ID NO: 1 or SEQ ID NO: 3 relates to the CRE 3 resistance gene of *Triticum tauschii* which controls resistance to cyst nematodes Heterodera sp. Preferably, the cyst nematode is the cereal cyst nematode (CCN) *Heterodera avenae*. The designation "CRE 3" is also synonymous with the designation "Ccn-D1" referred to by Eastwood et al. (1993), among others.

A further aspect of the present invention contemplates a nucleic acid molecule which encodes a protein that confers or otherwise facilitates nematode resistance in a plant and which is capable of hybridising under at least low stringency conditions to the nucleic acid molecule set forth in SEQ ID NO: 1 and/or SEQ ID NO: 3.

For the purposes of defining the level of stringency, a low stringency is defined herein as being a hybridisation and/or a wash carried out in 6xSSC buffer, 0.1% (w/v) SDS at 28° C. Generally, the stringency is increased by reducing the concentration of SSC buffer, and/or increasing the concentration of SDS and/or increasing the temperature of the hybridisation and/or wash. Conditions for hybridisations and washes are well understood by one normally skilled in the art. For the purposes of clarification of parameters affecting hybridisation between nucleic acid molecules, reference can conveniently be made to pages 2.10.8 to 2.10.16. of Ausubel et al. (1987), which is herein incorporated by reference.

Genetic analysis indicates that specific interactions may occur between resistance genes and gene products of the parasitic nematode. Although not intending to limit the present invention to any one theory or mode of action, it is proposed that the genetic sequences of the present invention control host range via specific recognition of the gene products of the nematode pest, in a "gene-for-gene" interaction that is understood by one normally skilled in the art. Accordingly, the genetic sequences are useful in increasing the range of resistance of a plant to nematode pests, by providing de novo the required nematode resistance gene, or being introduced together with the corresponding nematode gene or genes, on, for example, a single genetic cassette. Accordingly, these aspects of the invention are covered by the expression "conferring, improving, or otherwise enhancing nematode resistance" or other similar expression.

The present invention is particularly directed to resistance that is conferred, enhanced, or facilitated against a nematode, preferably a cereal cyst nematode, more preferably *Heterodera avenae*, by a polypeptide encoded by genetic sequences from *Triticum tauschii*. Examples of genetic sequences in *Triticum tauschii* which confer resistance to a nematode include, but are not limited to the Ccn genes, Ccn-D1 and Ccn-D2. The subject invention clearly contemplates other sources of nematode resistance genes, such as but not limited to, other monocotyledonous plants, other Triticum sp., barley, maize, rye, oats, and rice, amongst others.

The genetic sequences which encode a protein which confers, enhances, or otherwise facilitates nematode resistance may correspond to the naturally occurring sequence or may differ by one of or more nucleotide substitutions, deletions and/or additions. Accordingly, the present invention extends to nematode resistance genes and any functional genes, mutants, derivatives, parts, fragments, homologues or analogues thereof or non-functional molecules but which are at least useful as, for example, genetic probes, or primer sequences in the enzymatic or chemical synthesis of said gene, or in the generation of immunologically interactive recombinant molecules.

In a particularly preferred embodiment, the nematode resistance genetic sequences or like genetic sequences are employed to identify and isolate similar genes, or nematode resistance-like genes from other plants. The present invention extends to the use of said genetic sequence, or a part thereof to detect polymorphisms of a nematode resistance genetic sequence or nematode resistance-like genetic sequence.

In this aspect of the invention, there is provided an oligonucleotide molecule of at least 10 nucleotides in length capable of hybridising under low stringency conditions to part of the nucleotide sequence, or to a complement of the nucleotide sequence set forth in SEQ ID NO: 1 and/or SEQ ID NO: 3.

Accordingly there is contemplated a method for identifying a related nematode resistance genetic sequence or nematode resistance-like genetic sequence, said method comprising contacting genomic DNA, or mRNA, or cDNA, or parts, or fragments thereof, or a source thereof, with a hybridisation effective amount of a genetic sequence encoding or complementary to a genetic sequence encoding a polypeptide which confers, enhances or otherwise facilitates nematode resistance, or a part thereof, and then detecting said hybridisation.

The related nematode resistance genetic sequence or like sequence may be in a recombinant form, in a virus particle, bacteriophage particle, yeast cell, animal cell, or a plant cell. Preferably, the related genetic sequence originates from *Triticum aestivum* or similar plant such as maize, barley, rye, oats, or rice and/or wild varieties and/or hybrids or derivatives and/or ancestral progenitors of same. In addition, the related genetic sequence may be bound to a support matrix, for example nylon, nitrocellulose, polyacrylamide, agarose, amongst others.

Preferably, the genetic sequence which encode a polypeptide which confers, enhances, or otherwise facilitates nematode resistance (i.e. latter genetic sequence) is from Triticum sp., or similar plant such as maize, barley, rye, oats, or rice. In a most preferred embodiment, the latter genetic sequence is as set forth in SEQ ID NO: 1 and/or SEQ ID NO: 3.

Preferably, the latter genetic sequence is labelled with a reporter molecule capable of giving an identifiable signal (e.g. a radioisotope such as $^{32}P$ or $^{35}S$ or a biotintylated molecule).

An alternative method contemplated in the present invention involves hybridising a nucleic acid primer molecule of at least 10 nucleotides in length to a nucleic acid "template molecule", said template molecule herein defined as a nematode resistance genetic sequence, or resistance-like genetic sequence, or a functional part thereof, or its complementary sequence. Specific nucleic acid molecule copies of the template molecule are amplified enzymatically in a polymerase chain reaction, a technique that is well known to one skilled in the art.

Preferably, the nucleic acid primer molecule or molecule effective in hybridisation is contained in an aqueous mixture of other nucleic acid primer molecules. More preferably, the nucleic acid primer molecule is in a substantially pure form. In a preferred embodiment, the nucleic acid primer molecule is from Triticum sp., or similar plant such as maize, barley, rye, oats, or rice. In a most preferred embodiment, the nucleic acid primer molecule is any nucleotide sequence of at least 10 nucleotides in length derived from, or contained within the nucleotide sequence as set forth in SEQ ID NO: 1 and/or SEQ ID NO: 3.

The nucleic acid template molecule may be in a recombinant form, in a virus particle, bacteriophage particle, yeast cell, animal cell, or a plant cell. Preferably, the related genetic sequence originates from *Triticum aestivum* or similar plant such as maize, barley, rye, oats, or rice and/or wild varieties and/or hybrids or derivatives and/or ancestral progenitors of same.

A further aspect of the present invention is directed to a genetic construct comprising an isolated nucleic acid molecule which encodes or is complementary to a nucleic acid molecule which encodes a protein, or derivative thereof, that confers, enhances, or otherwise facilitates resistance against a nematode in a plant cell. Preferably, the gene sequence is related to or a functional derivative, part fragment, homologue, or analogue of the nucleotide sequence defined by SEQ ID NO: 1 and/or SEQ ID NO: 3.

The present invention extends to genetic constructs designed to assist expression of a nucleic acid molecule that confers, enhances or facilitates nematode resistance in a cell. Generally, the genetic construct comprises in addition to the subject nucleic acid molecule, a promoter and optional other regulatory sequences that modulate expression of the nucleic acid molecule. The promoter may be the CRE 3 gene promoter, or a promoter from another genetic source. Preferably, however, the promoter is capable of expression in a plant cell.

The subject nucleic acid molecule may be genomic DNA or cDNA and may correspond in sequence exactly with the nucleotide sequence as set forth in SEQ ID NO: 1 and/or SEQ ID NO: 3, or it may contain one or more nucleotide substitutions, additions and/or deletions, either dispersed throughout, or clustered.

In an alternative embodiment, an isolated promoter sequence from a gene which, when expressed encodes a polypeptide that confers, enhances or otherwise facilitates nematode resistance in a cell, or a functional part, derivative, fragment, homologue or analogue thereof, is operably linked to the coding region of a second genetic sequence, for example the β-glucuronidase gene, or the chloramphenicol acetyltransferase gene, or the firefly luciferase gene, amongst others. Preferably, the promoter sequence is contained within the sequence set forth in SEQ ID NO: 1.

Yet another aspect of the present invention provides for the expression of the subject genetic sequence in a suitable host (e.g. a prokaryote or eukaryote) to produce full length or non-full length recombinant nematode resistance gene products. Preferably, the nematode resistance gene product has a sequence that is identical to, or contained within the amino acid sequence set forth in SEQ ID NO: 2 and/or SEQ ID NO: 4. The present invention extends also to a synthetic peptide fragment of a nematode resistance gene product, preferably the resistance gene product set forth in SEQ ID NO: 2 and/or SEQ ID NO: 4.

The present invention provides an isolated polypeptide which comprises an amino acid sequence which confers, enhances, or otherwise facilitates resistance to a nematode in a plant cell, or a functional mutant, derivative part, fragment or analogue of said polypeptide.

According to this aspect, the present invention also extends to the protein or polypeptide product of the *Triticum tauschii* nematode resistance gene Cre3 and the weaker resistance gene Ccn-D2. This is done, however, with the understanding that the subject invention extends to a range of resistance genes for nematode and other pathogens. In fact, the present invention extends to a nematode resistance gene characterised by said gene encoding a product having at least one imperfect leucine rich repeat region. Preferably, the leucine rich repeat region is located at the C-terminal end of the protein molecule and has at least 60% similarly to amino acid residues 228 to 412 of the amino acid sequence set forth in SEQ ID NO: 4, and even more preferably at least 80% similarity. Still more preferably, the leucine rich region corresponds to amino acid residues 185 to 412 of the amino acid sequence set forth in SEQ ID NO: 4.

Alternatively or in addition to, the nematode resistance gene product further contains a p-Loop, or kinase-1a motif, near the N-terminus of the amino acid set forth in SEQ ID NO: 2, and having the sequence:

GVGGSGKST, and more particularly

GIHGVGGSGKST, or having one or more amino acid substitutions, insertions and/or deletions thereto provided that such derivatives still function as a p-Loop in conferring nematode resistance in a cell. A p-Loop is involved in ATP/GTP binding.

Alternatively, or in addition to, the nematode resistance gene product further contains a kinase-2 motif, near the N-terminus of the amino acid sequence set forth in SEQ ID NO: 4, and having the sequence:

XXXXD, where X is any hydrophobic amino acid residue, and more particularly:

KLDGKRFLLILDDVWC, or having one or more amino acid substitutions, deletions, and/or insertions thereto provided that such derivatives still function as a kinase-2 motif. A kinase-2 motif functions in nucleotide binding, preferably in binding of ATP/GTP.

The present invention extends to a recombinant gene product that contains the p-Loop, and/or kinase-2, and/or imperfect leucine-rich repeat sequence in any relative combination, or frequency, provided that said recombinant gene product confers, enhances, or facilitates nematode resistance in a cell.

The present invention also extends to a synthetic peptide comprising any part of the amino acid sequence set forth in SEQ ID NO: 2 and/or SEQ ID NO: 4, or having at least 40% similarity to all or a part thereof.

The recombinant nematode resistance gene product, nematode resistance-like gene product, or functional derivative thereof, may be used to produce immunologically interactive molecules, such as antibodies, or functional derivatives thereof, the only requirement being that the recombinant products are immunologically interactive with antibodies to all or part of said gene product.

According to this aspect, there is provided an antibody that binds to a polypeptide comprising an amino acid sequence which:

(i) confers, enhances, or otherwise facilitates resistance to a nematode in a plant; or (ii) is substantially the same as the amino acid sequence set forth in SEQ ID NO: 2 and/or SEQ ID NO: 4, or having at least 40% similarity to all or a part thereof.

Antibodies to a recombinant nematode resistance gene product are particularly useful in the screening of plants for the presence of said gene product. Another aspect of the present invention is, therefore, directed to antibodies to a recombinant nematode resistance gene product or part or fragment thereof. Such antibodies may be monoclonal or polyclonal and may be selected from naturally occurring antibodies to a nematode resistance gene product or may be specifically raised to a recombinant nematode resistance gene product. In the case of the latter, the nematode resistance gene product may first need to be associated with a carrier molecule. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies and/or the recombinant nematode resistance gene products of the present invention are particularly useful for the immunological screening of nematode resistance gene products in various plants, in monitoring expression of nematode resistance genetic sequences in transgenic plants and as a proprietary tagging system.

In one embodiment, specific antibodies are used to screen for nematode resistance gene products or nematode resistance-like gene products in plants. Techniques for the assays contemplated herein are known in the art and include, for example, sandwich assays and ELISA.

It is within the scope of this invention to include any second antibodies (monoclonal, polyclonal or fragments of antibodies) directed tot he first mentioned antibodies discussed above. Both the first and second antibodies may be used in detection assays or a first antibody may be used with a commercially available anti-immunoglobulin antibody. An antibody as contemplated herein includes any antibody specific to any region of a recombinant nematode resistance gene product.

Both polyclonal and monclonal antibodies are obtainable by immunisation with a recombinant nematode resistance gene product and either type is utilisable for immunoassays. The methods of obtaining both types of sera are well known in the art. Polyclonal sera are less preferred but are relatively easily prepared by injection of a suitable laboratory animal with an effective amount of recombinant nematode resistance gene product, or antigenic or immunointeractive parts thereof, collecting serum from the animal and isolating specific sera by any of the known immunoadsorbent techniques. Although antibodies produced by this method are utilisable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitised against the immunogenic preparation can be done by techniques which are well known to those who are skilled in the art (see, for example, Douillard and Hoffman, 1981; Kohler and Milstein, 1975; Kohler and Milstein, 1976).

The presence of a nematode resistance gene product or nematode resistance-like gene product in a plant or more commonly plant extract may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilised on a solid substrate and the sample to be tested brought into contact with the bound molecule. After a suitable period of incubation, for a period of time and under conditions sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule.

In this case, the first antibody is raised to a recombinant nematode resistance gene product and the antigen is a nematode resistance gene product in a plant.

The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain nematode resistance gene product and include crude of purified plant extract such as extracts of leaves, roots and stems.

In the typical forward sandwich assay, a first antibody raised against a recombinant nematode resistance gene product is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking, covalent binding or physically adsorption, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any antigen present in the sample to the antibody. Following the incubation period, the reaction locus is washed and dried and incubated with a second antibody specific for a portion of the first antibody. The second antibody is linked to a reporter molecule which is used to indicate the binding of the second antibody to the hapten.

An alternative method involves immobilising the target molecules in the biological sample and then exposing the immobilised target to specific antibody which may or may not be labelled with a reporter molecule. Depending on the amount of target and the strength of the reporter molecule signal, a bound target may be detected by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognised, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a flurescent product rather than the chromogenic substrates noted above. In all cases, the enzyme-labelled antibody is added to the first antibody-hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. The term "reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in enzyme immunoassays (EIA), the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

It will be readily apparent to the skilled technician how to vary the above assays and all such variations are encompassed by the present invention.

The present invention further extends to a plant such as a crop plant carrying a non-endogenous nucleic acid molecule encoding or complementary to a nucleic acid molecule encoding a polypeptide which confers, enhances, or otherwise facilitates nematode resistance in said plant. Preferably, the plant is a monocot plant. More preferably the transgenic plant is one or more of the following: *Triticum aestivum, Triticum tauschii,* maize, barley, rye, oats, rice, sorghum, amongst others. Other species are not excluded.

The non-endogenous genetic sequence or transgene may originate from any plant species. Preferably, said genetic sequence is identical to the nucleotide sequence set forth in SEQ ID NO: 1 and/or SEQ ID NO: 3, or a functional derivative, fragment, part, homologue, or analogue thereof.

Further, the said genetic sequence or transgene may be placed operably under control of the Cre3 promoter sequence, or under the control of a heterologous promoter sequence. The expression of the transgene may be constitutive or inducible by an external stimulus such as physiological stress, or by addition of a chemical compound, or the expression may be developmentally-regulated, or expressed in a tissue- or cell-specific pattern. Furthermore the transgene may be inserted into or fused to a particular endogenous genetic sequence.

A non-endogenous nucleic acid molecule encoding, or complementary to a nucleic acid molecule encoding a polypeptide which confers, enhances or otherwise facilitates nematode resistance in a recipient plant may be introduced into said plant by any one, or a combination of procedures, including Agrobacterium-mediated transformation, microparticle bombardment, PEG fusion, electroporation, introgression via conventional breeding program, amongst others. It will be readily apparent to one skilled in the art how to produce plants carrying a non-endogenous genetic sequence and perform variations to said procedures.

The present invention extends to the progeny and clonal derivatives of said plant.

The present invention is further described in the following Examples. The embodiments exemplified hereinafter are in no way to be taken as limiting the subject invention.

EXAMPLE 1

Plant Material

Experiments were conducted in four resistant and three susceptible accessions of *Triticum tauschii,* as indicated in Table 2.

TABLE 2

Parental *Triticum tauschii* lines used to create crosses for bulked segregant analysis

| Accession | Taxon | Reaction to *Heterodera avenae* |
| --- | --- | --- |
| AUS 18912 | ssp. *eusquarrosa* var. meyeri | resistant (Ccn-D1) |
| AUS 18913 | ssp. *eusquarrosa* var. meyeri | resistant (Ccn-D1) |
| CPI 110810 | ssp. *eusquarrosa* var. typica, intermediate | resistant (Ccn-D1) |
| CPI 110813 | ssp. *eusquarrosa* var. typica, intermediate | resistant (Ccn-D2) |
| CPI 110856 | ssp. *eusquarrosa* var. typica | susceptible |
| CPI 110825 | Intermediate | susceptible |
| CPI 110795 | Intermediate | susceptible |

The four segregating progeny analysed were from the following crosses:

1. CPI 110813×CPI 110795
2. CPI 110810×CPI 110825
3. AUS 18913×CPI 110856
4. AUS 18912×CPI 110856

Segregation for resistance to the nematode *Heterodera avenae* was determined for the F2 progeny of each cross and for 10–12 individuals within each F3 family. A total of 2472 individuals were assessed for reactions to *Heterodera avenae*. Fifty eight to sixty two F2 plants from each cross were chosen on the basis of availability of F3 data and recovery of sufficient DNA to determine market segregation. Chromosomal locations of polymorphic DNA markers were determined by nullitetrasomic and ditelocentric lines of *Triticum aestivum* cv. Chinese Spring and wheat-barley addition lines (Islam et al., 1981; Sears, 1966).

EXAMPLE 2

Plant Resistance

Resistance to the nematode *Heterodera avenae* was assessed using the method of Eastwood et al. (1991), except that the white female nematodes were washed from the roots onto a 300 micron sieve, decanted from the sand and counted under a magnifying lamp.

The F3 families in crosses 2,3,4 (see Table 2) segregated for reaction to *Heterodera avenae* at the Ccn-D1 locus in the ratio 1:2:1 (homozygous resistant: heterozygous resistant: homozygous susceptible), consistent with the ratio expected for Mendelian inheritance of a single dominant autosomal gene.

An average of $0.14\pm0.1$ white females (cysts) were produced per homozygous resistant Ccn-D1 plant, compared to $1.38\pm0.46$ (range 0–8) per resistant line homozygous for the weaker Ccn-D2 gene. The susceptible lines carried a significantly greater number of cysts, in the range of 10–90 cysts.

EXAMPLE 3

RFLP Segregation Analysis

The prior art teachings of Andersen and Andersen (1973), Slootmaker et al. (1974), Rivoal et al. (1986), and Aseidu et al. (1990) indicated the presence of resistance loci to *Heterodera avenae* on group 2 and group 6 homeologous chromosomes of bread wheat *Triticum aestivum*. One-half of the 60 RFLP markers used were selected because they map to these chromosome locations, thus maximising the probability of selecting an RFLP linked to the Ccn loci.

A total of b 35RFLP were analysed for linkage to Ccn-D2 using the segregants from cross 1, and 34 loci for linkage to Ccn-D1, using the segregants from cross 2. A total of 17 polymorphic loci were identified on groups 2 and 6 chromosomes, of which 11 segregated with the Ccn-D1 locus and 6 segregated with the Ccn-D2 locus.

Multipoint analysis of joint F2/F3 segregation of RFLP loci and Ccn resistance revealed a loose linkage between Ccn-D2 and chromosome 2 markers (FIG. 1). No methods used were able to identify polymorphisms to map further, the Ccn-D2 locus.

Two-point RFLP linkage data set for cross 1 showed 5 cM map units between Ccn-D2 resistance and the RFLP markers ksuH9 (Gill et al., 1991) and csIH52 (Lagudah et al., 1993), where 1 cM is herein defined as 1% recombination between two genetic loci or markers, in a randomly segregating population. Ccn-D1 was linked to ksuH9 only (FIG. 1).

EXAMPLE 4

PCR Amplification of DNA from Bulked F2 Segregants to Identify DNA Products Linked to Ccn-D1

Parental lines and individuals $F_2$ plants were processed for the isolation of leaf DNA as described in Lagudah et al.

(1991). Bulked DNA pools for resistance and susceptibility to *Heterodera avenae* were generated from $F_2$ populations from cross 2 and cross 3 (Table 2). Pooled samples from cross 2 were created by bulking together DNA from 12 homozygous resistant and 13 homozygous susceptible $F_2$ lines, and in cross 3 from 10 resistant and 13 susceptible homozygotes. Two hundred micrograms of genomic DNA from each sample was sonicated for 6 seconds to give a size range of 0.5–6 kb (Clarke et al. 1992). A second set of unsonicated bulked DNA segregants from population 3 was included in the study. Each sample was ethanol precipitated and resuspended in 400 µL of 0.12 M phosphate buffer (pH 6.8).

Molecular markers were generated from bulked homozygous resistant and susceptible F2 DNA pools of cross 2 (Table 2), by PCR amplification of genomic DNA using 260 random 10-mer oligonucleotides (Operon Technologies, Alameda, Calif.) (OPA-01 to OPM 20). Other oligonucleotides included were 4 semirandom primers of 15–18 nucleotides in length, based on the consensus nucleotide sequences of intron-exon splice junctions for plant genes (Weining and Langridge, 1991), designated ISJR1, ISJR2, ISJE3 and ISJE4.

PCRs were performed in 10 µL of a reaction mix containing about 30 ng of template DNA, 0.5 units of Taq polymerase (Boehringer Mannheim GMBH, Germany), 15 ng of primer, 1.5 mM $MgCl_2$ and 1 x reaction buffer (0.2 mM dNTPs, 67 mM Tris-HCl (pH 8.8), 16 nM $(NH_4)_2 SO_4$ 0.01% (w/v) gelatin, and 0.45% (v/v) Triton X-100). Samples were loaded into capillary tips and run on a thermocycler (FTS-1 Thermal Sequencer, Corbett Research, Sydney, Australia) under the following conditions:

1. Five cycles of denaturation at 93° C. for 30 seconds, annealing at 35° C. for 120 seconds, and extension at 72° C. for 90 seconds; and
2. Thirty five cycles of denaturation at 92° C. for 5 seconds, annealing at 40° C. for 20 seconds, and extension at 72° C. for 90 seconds; and
3. One cycle of denaturation at 92° C. for 10 seconds, annealing at 40° C. for 20 seconds, and extension at 72° C. for 5 minutes. When longer and specific oligonucleotide (24 bases) primer pairs were used the annealing temperature was 55° C.

The reaction products were visualised in 1.5% (w/v) agarose gels containing ethidium bromide, using UV light.

EXAMPLE 5

Fractionation of DNA to Enrich for Low-Copy Sequences

Wheat genomic DNA has a large proportion of highly-repeated DNA sequences, which may reduce the probability of detecting low-copy sequences in the genome, using PCR. To improve the intensity of the PCR band generated using ISJE3, DNA was fractionated on hydroxylapatite to remove highly repetitive DNA sequences.

Enrichment for low copy sequences from total genomic DNA was achieved by reannealing the heat denatured DNA (100° C. for 10 minutes) at 61° C. for at least 20 hours to a C (=moles nucleotide/liter×incubation time [seconds]) value of greater than 100 (Smith and Flavell, 1975). Resistant and susceptible bulks in segregants of cross 2 (Table 2) were annealed to a C value of 145, while those in bulked segregants of cross 3 were annealed for a C value of 120. The samples were then loaded into a 10 mm diameter hydroxylapatite (Biorad DNA grade, Bio-gel HTP) column maintained at 60° C. that had been prewashed with several volumes of 0.01M phosphate buffer (pH 6.8). The column was rinsed with 3 mL of 0.01M phosphate buffer and the single-stranded DNA as eluted with one column volume of 0.15M phosphate buffer (60° C.) and collected in 16×0.5 mL aliquots. The DNA concentration in each aliquot was determined with UV (260 nm) spectrophotometry and three to four of the 0.5 mL aliquotes that contained most of the DNA were further concentrated with butan-2-ol extractions (Sambrook et al. 1989) and each sample of three to four tubes finally reduced to a single sample of 100–120 µL. Sodium phosphates were removed from the DNA using a Sephadex 50 column equilibrated with TEN buffer (10 mM Tris, 1 mM EDTA, 100 mM NaCl, pH 8.0). DNA was recovered by ethanol precipitation and diluted to a concentration of 300 ng/µL in TE ready for use in PCR amplification reactions.

The average proportion of DNA recovered after hydroxylapatite fractionation in bulked segregants from cross 2 and cross 3 was 17% and 25%, respectively.

EXAMPLE 6

Figure 2:
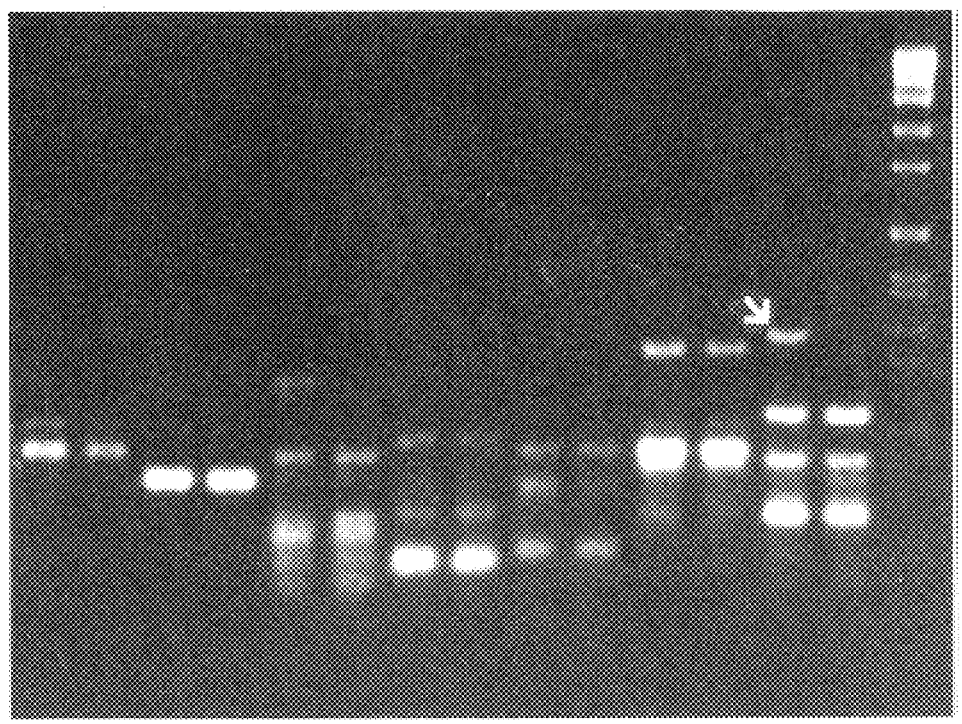
FIG. 2 is a photographic representation of an agarose gel showing PCR amplification products obtained from a survey of hydroxylapatite-fractionated DNA enriched for low copy sequences. DNA samples were from bulked segregants of the *Triticum tauschii* cross CPI 110810 (resistant)×CPI 110825 (susceptible). Odd-numbered lanes contain DNA from resistant bulked segregants. Even-numbered lanes contain DNA from susceptible bulked segregants. Random primers used for each pair were OPF12 (lanes 1,2), OPF13 (lanes 3,4), OPG2 (lanes 5,6), OPG3 (lanes 7,8), OPG6 (lanes 9,10), OPG6 (lanes 11,12) and OPG13 (lanes 13,14). The arrow indicates the presence of a polymorphic PCR fragment present in lane 13 but absent from lane 14. Lane 15 is a size marker.

PCR Amplification of DNA Enriched for Low-Copy Sequences from Bulked F2 Segregants Polymorphic amplification products were obtained using four random 10-mer primers, including ISJE3, in the bulked segregants of cross 2 (see Table 2), an increase in the detectable level of polymorphism from 0.45% to 2%. In each case, the polymorphic PCR product obtained was associated with the presence of a DNA band in the resistant bulk, that was absent from the susceptible bulk (FIG. 2).

Figure 3:
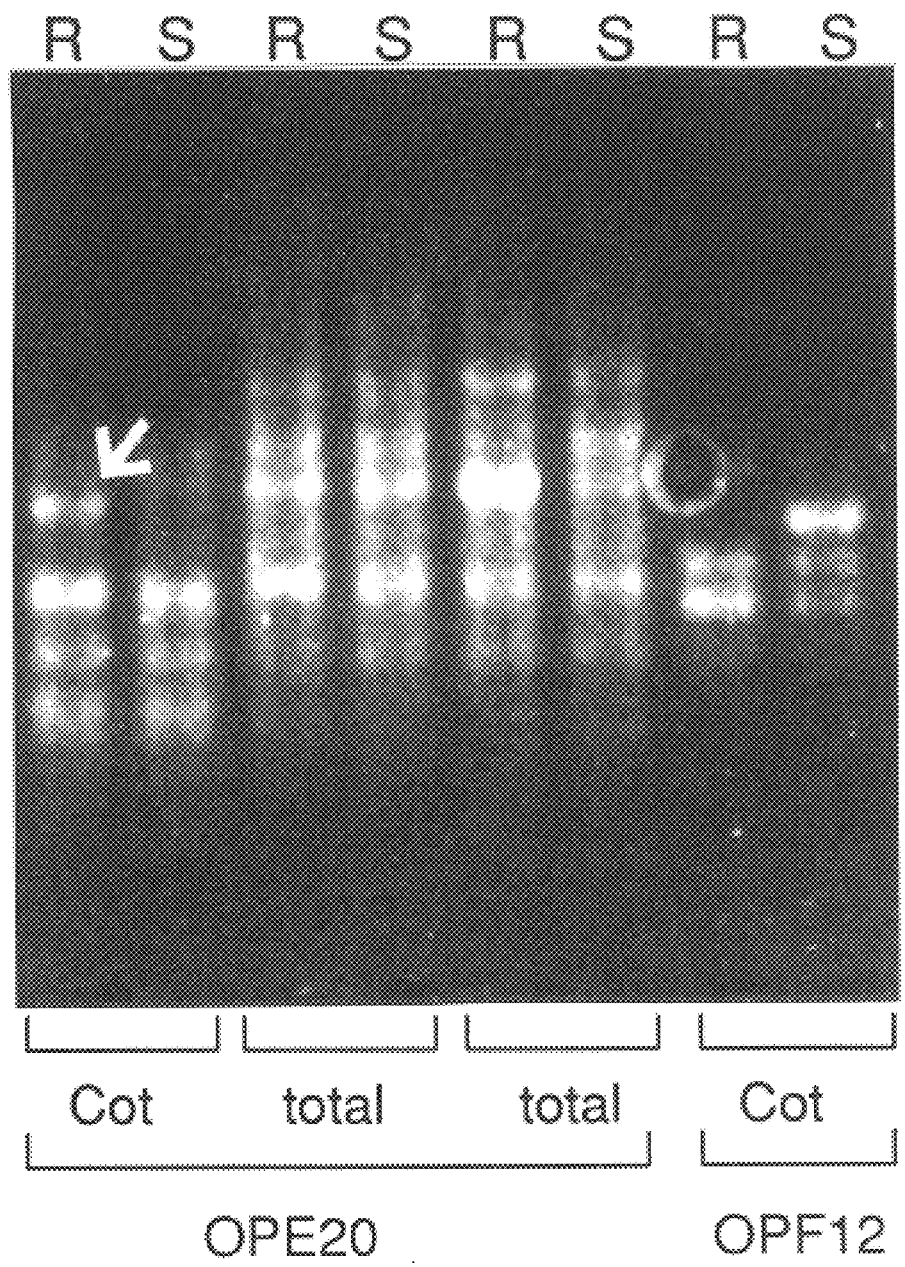
FIG. 3 is a photographic representation of an agarose gel showing PCR amplification products obtained from total genomic DNA and hydroxylapatite-fractionated DNA enriched for low copy sequences. DNA samples were from parental and bulked segregants of the *Triticum tauschii* cross AUS 188913 (resistant)×CPI110856 (susceptible). Amplification products were obtained using the random primers OPE20 (lanes 1–6) and OPF12 (lanes 7,8). Templates were from low copy bulked resistant segregant (lanes 1,7), low copy bulked susceptible segregant (lanes 2,8), total genomic bulked resistant segregant (lane 3), total genomic bulked susceptible segregant (lane 4), total genomic from AUS 188913 (lane 5), and total genomic from CPI 110856 (lane 6). The arrow indicates the presence of a polymorphic PCR fragment present in resistant bulked segregant (lane 1) but not in the susceptible bulked segregant (lane 2). The converse type of polymorphism is shown with primer OPF 12 in lanes 7 and 8.

Polymorphic amplification products were also obtained using eight random 10-mer primers, in the bulked segregants of cross 3 (Table 2). In seven of the polymorphisms, the polymorphic PCR product was associated with the susceptible bulk and only one (OPE-20) was associated with the resistant bulk (FIG. 3). Primer OPE-20 produced a consistent polymorphisms in DNA enriched for low-copy nucleotide sequences, but not for total wheat genomic DNA of either the parental genotypes, or the bulked segregating progeny (FIG. 3).

EXAMPLE 7

Chromosome Location and Genetic Linkage of Polymorphic PCR Products

The polymorphic PCR products present in the resistant bulk plus the DNA amplified in the susceptible bulk using primer OPF12 (FIG. 2, FIG. 3) were excised from low-melting agarose gels, radiolabelled and hybridised to membrane filters containing DNA of parental lines from all populations that had been digested with restriction enzymes.

Polymorphism was observed using a 1 kb amplified DNA fragment, designated E-20. All Ccn-D1 resistant parents showed one to two major hybridising DNA fragments, while the susceptible lines were characterised by a single minor hybridising fragment. The E-20 fragment was subsequently cloned into a "T-overhang" pUC118 plasmid vector, to produce the recombinant plasmid csE20-2.

Genomic and cDNA clones used in the construction of *Triticum tauschii*, wheat, and barley genetic maps (Sharp et al., 1989; Gill et al., 1991; Lagudah et al., 1991a; Heun et al., 1991), as well as the csE20-2 clone were used as RFLP markers to analyse joint segregation with CCN resistance/susceptibility in the $F_2$ progenies. Procedures for RFLP analysis were as described by Lagudah et al. (1991a). As an aid in selecting potential markers to target the CCN resistance region, the genetic map of *Triticum tauschii* produced from the main mapping population (cross F) reported by Lagudah et al. (1991, 1993) was aligned with common reference RFLP loci mapped in the CCN population (FIG. 1). Linkage analysis of segregating RFLP loci and CCN resistance derived from all F2 progenies were carried out using the MAPMAKER program (Lander et al., 1987).

Figure 4:
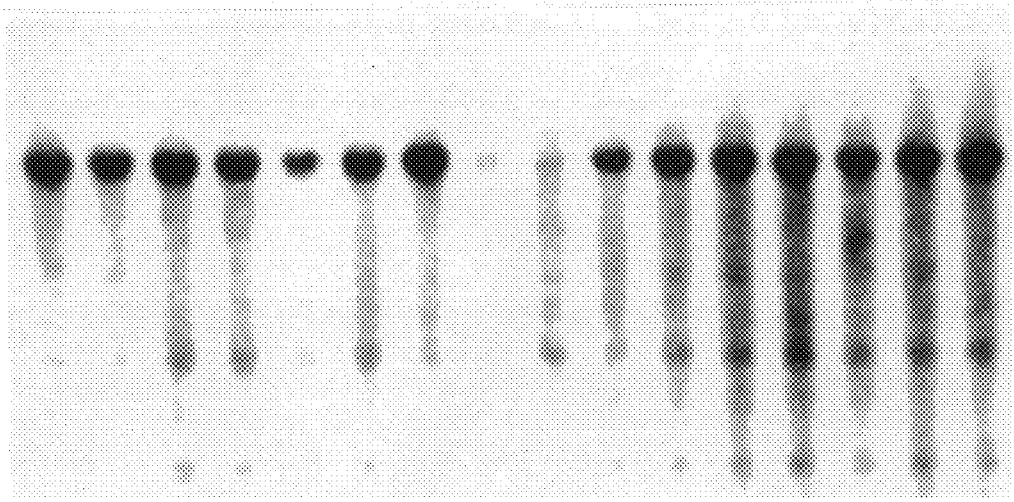
FIG. 4 is a photographic representation showing an autoradiograph of one cuploid (lane 1) and several nullitetrasomic lines (lanes 2–6) of *Triticum aestivum* cv Chinese Spring, showing RFLP patterns assayed with the closed PCR fragment csE20-2. Cytogenetic stocks missing chromosome 2D are present in lanes 8 (nulli 2D tetra 2A) and 9 (nulli 2D tetra 2B).

Digested DNA from nullitetrasomic and ditelocentric lines of *Triticum aestivum* cv Chinese Spring were hybridised with the csE20-2 fragment, to determine its chromosome location. The csE-20-2 hybridising band was present in all lines except those deleted for chromosome 2D (FIG. 4), including the ditelo 2DS line, indicating that the csE-20-2 clone maps to the long arm of chromosome 2D.

Figure 5:
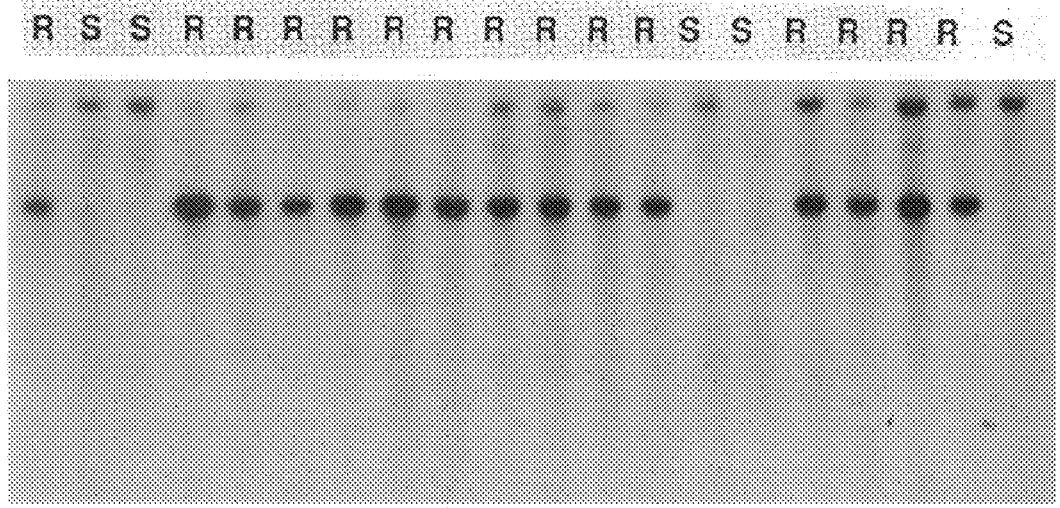
FIG. 5 is a photographic representation showing an autoradiograph of *Triticum tauschii* F2 individuals from the cross AUS 188913 (resistant)×CPI 110856 (susceptible) assayed with the cloned PCR fragment csE20-2. Ccn-D1 resistance (R) and susceptibility (S) are indicated.

The csE20-2 RFLP patterns of parental genotypes of *Triticum tauschii* and resistance or susceptibility to *Heterodera avenae* infestation reveal a complete linkage between Ccn-D1 and the csE20-2 RFLP marker, for segregating progeny of crosses 2,3, and 4 (Table 2, see FIG. 5). Pooled crosses were based on the RFLP analysis of 178 F2 lines and the *Heterodera avenae* reactions observed for 2020 individual F3 plants.

Further RFLP markers were mapped on chromosome 2D, in cross 3. As shown in FIG. 1b, both Ccn-D1 and csE20-2 are approximately 13.8 cM from the RFLP marker WG645 (Kleinhofs et al. 1993), 26.3 cM from csIH57-1 (Lagudah et al., 1991b), and 56.1 cM from ksu H9 (Gill et al., 1991), which have previously been localised on the long arm of chromosome 2. The Ccn-D1 parent CPI 110813 was mapped in cross 1, and the RFLP variant of csE20-2 shown also to be linked distally, 25 cM from csIH57-1, but independent of the Ccn-D2 locus (FIG. 1), suggesting the Ccn-D1 and Ccn-D2 are non-allelic nematode resistance genes.

EXAMPLE 8

Introgression of the Cre3 Gene Into Bread Wheat, *Triticum tauschii*

The Cre3 gene from *Triticum tauschii* was introgressed into bread wheat *Triticum aestivum* by repeated backcrossing to produce backcross one F4 lines. The csE20-2 RFLP marker was used as a probe to check for linkage among 30 progeny lines, between csE-20 and reaction to *Heterodera avenae* (FIG. 6). The 6.5 kb RFLP fragment detectable by hybridisation with csE-20 in resistant parental lines of *Triticum tauschii*, was observed in all resistant homozygous and heterozygous progeny of *Triticum aestivum* (FIG. 6, lanes 4,7,9,14,15). In contrast, bread wheat lines that were susceptible to infestation with *Heterodera avenae* all lacked the 6.5 kb RFLP fragment and exhibited identical RFLP patterns to the parental susceptible line (FIG. 6, lanes 3,5,6,8,10,11,12,13,16,17).

Thus, the introgressed Cre3 gene was able to confer nematode resistance in bread wheat, *Triticum aestivum*.

EXAMPLE 9

Positional Cloning of the Cre3Gene

Data from bulked segregant analysis provide indications of the genetic distance between loci, but no indication of the physical distance, in kb, which may be in the order of several megabases in a highly recombinogenic region such as the 2DL chromosome of *Triticum tauschii*. To determine the physical size (kb) per unit of genetic recombination (cM) in the Cre3 gene region, a series of chromosome deletion lines for the long arm of chromosome 2D (Endo, 1990) were employed. Genetic data from one deletion line, with 24% of the 2DL chromosome deleted, indicated that there were approximately 300 kb of DNA per cM in the Cre3 region of 2DL. Southern analysis on 178 F2 families, using the csE20-2 RFLP marker as a probe, showed complete cosegregation between Cre3 and the 6.5 kb EcoRV RFLP band that hybridises to csE20-2 (0.0% recombination, p=0.05). Thus, the Cre3 gene was estimated to be within 15 kb of csE20-2.

Figure 7:
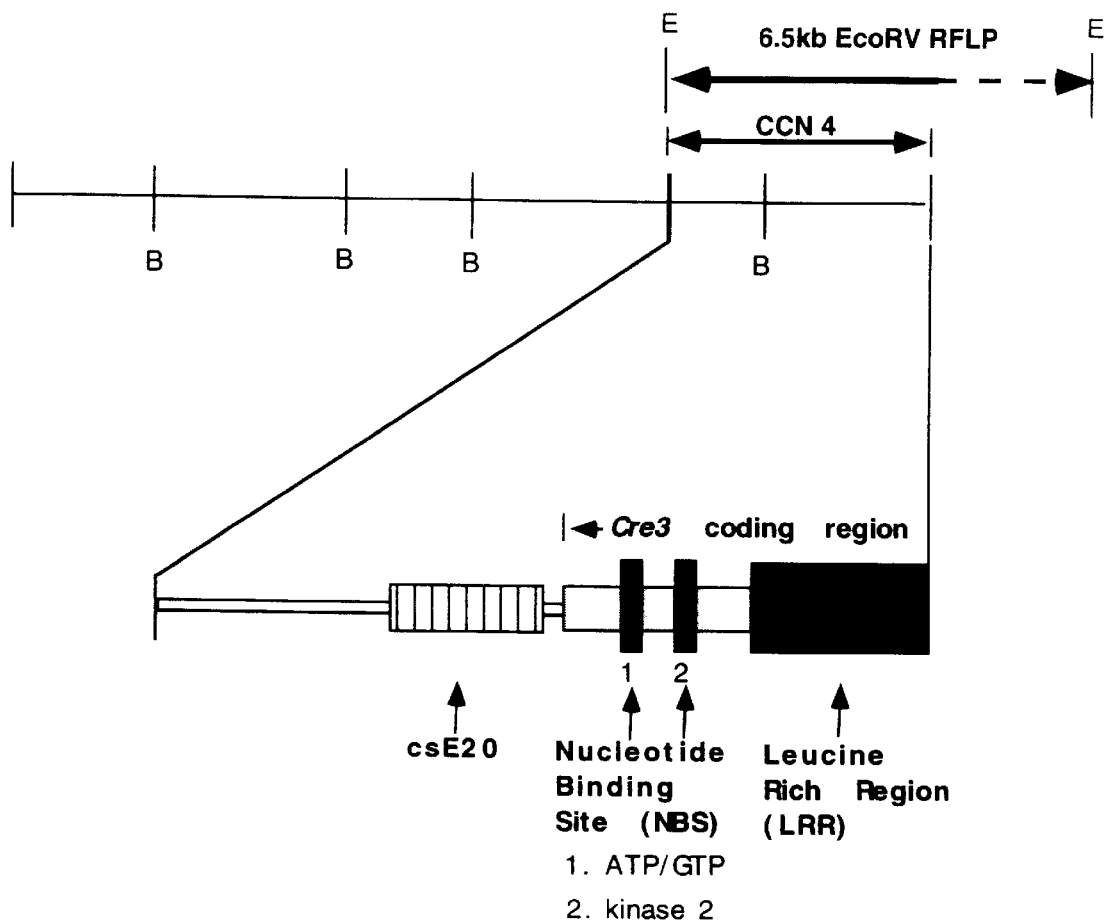
FIG. 7 is a schematic representation of a lambda clone containing the Cre3 gene. The positions of the 6.5 kb EcoRV RFLP fragment and PCR fragment csE20-2 are indicated. The position of the Cre3 gene within the lambda clone is also indicated. Restriction enzyme sites BamHi(B) and EcoRV(E) are indicated.

DNA from *Triticum tauschii* line AUS 18913 carrying the Cre3 gene, was size-fractionated to isolate fragments in the range 15–20 kb in length, and used to construct a lambda genomic library. The insert from csE20-2 was radioactively labelled and used to isolate three genomic clones, which were sub-cloned for further analysis. One sub-clone, designated CCN4, was shown to overlap 4 kb at the 5' end of the 6.5 kb EcoRV RFLP band (FIG. 7). This subclone was also shown to cosegregate with Ccn resistance.

The sequenced region of CCN4 clone contains the nucleotide sequences of the 889 bp PCR amplification product E-20, between nucleotide positions 194 and 1082 of the nucleotide sequence set forth in SEQ ID NO: 1. The sequenced region of CCN4 also contains two overlapping reading frames (exons) from nucleotides 1138 to 1614 of the nucleotide sequence set forth in SEQ ID NO: 1 and from nucleotides 1 to 1238 of the nucleotide sequence set forth in SEQ ID NO: 3, with no stop codon at the end of the second exon, suggesting that the clone contains a partial Cre3 gene sequence.

The first exon encodes a p-Loop (or kinase-1a) motif between nucleotides 1414 and 1347 of the nucleotide sequence set forth in SEQ ID NO: 1, with the amino acid sequence GVGGSGKS. The second exon encodes another nucleotide binding site, kinase-2, between nucleotide positions 73 and 87 and an imperfect leucine-rich repeat sequence from nucleotides 682 to 1238 of the nucleotide sequence set forth in SEQ ID NO: 3.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Andersen, S. and Andersen, K. (1973). Linkage between marker genes on barley chromosome 2 and a gene for resistance to *Heterodera avenae*. Hereditas, 73: 271–276.

2. Asiedu, R., Fisher, J. M., and Discoll, C. J. (1990). Resistance to *Heterodera avenae* in the rye genome of triticale. Theor. Appl. Genet, 79:331–336.

3. Ausubel, F. M., Brent, R., Kingston, R. E., Moore, D. D., Seidman, J. G., Smith, J. A., and Struhl, K. (1987). Current Protocols in Molecular Biology. Wiley Interscience (ISBN 047150338)

4. Clarke, B. C., Stancombe, P., Money, T., Foote, T. and Moore, G. (1992). Targeting deletion (homoeologous chromosome pairing locus) or addition line single copy sequences from cereal genomes. Nucleic Acids Res. 20:1289–1292.

5. Douillard and Hoffman (1981). Basic Facts about Hybridomas. In: Compendium of Immunology Vol II (ed. Schwarz)

6. Eastwood, R. F., Lagudah, E. S., Appels, R., Hannah, M. and Kollmorgen, J. F. (1991). *Triticum tauschii*: A novel source of resistance to cereal cyst nematode (*Heterodera avenae*). Aust. J. Agric. Res. 42:69–77.

7. Eastwood, R. F., Lagudah, E. S. Halloran, G. M., Brown, J. S., Kollmorgen, J. F. and Appels, R. (1993). Resistance to cereal cyst nemotodes in *Triticum tauschii*. In: Proceedings of the 10th Australian Plant Breeding Conference. (B.C. Imrie and J. B. Hacker eds) pp. 7–9.

8. Endo, T. R. (1990). Gametocidal chromosomes and the induction of chromosome mutations in wheat. Jap. J. Genetics, 65: 135–152

9. Gill, K. S., Lubbers, E. L., Gill, B. S., Raupp, W. J. and Cox, T. S. (1991). A genetic linkage map of *Triticum tauschii* (DD) and its relationship to the D genome of bread wheat (AABBDD). Genome, 34:830–839.

10. Heun, M., Kennedy, A. E., Anderson, J. A., Lapitan, N. L. V., Sorrells, M. E. and Tranksley, S. D. (1991). Construction of a restriction fragment length polymorphism map for barley (*Hordeum vulgare*). Genome, 34:437–447.

11. Islam, A. K. M. R., Shephered, K. W. and Sparrow, D. B. H. (1981). Isolation and addition of euplasmic wheat-barley addition lines. Heredity, 46:161–174.

12. Kleinhofs, A., Kilian, A., Saghai-Maroof, M. A., Biyashev, R. M., Hayes, P., Chen, F. Q., Lapitan, N., Fenwick, A., Blake, T., Kamazin, V., Ananiev, R., Dahleen, L., Kudma, D., Bollinger, J., Knapp, S. J., Liu, B., Sorrells, M., Heun, M., Frankwiak, J. D., Hoffamn, D., Skadsen, R. and Steffenson, B. J. (1993). A molecular isozyme and morphological map of barley (*Hordeum vulgare*). Theor. Appl. Genet. 86: 705–712.

13. Kohler and Milstein (1975). Nature, 256: 495–499

14. Kohler and Milstein (1976). Eur.J. Immunology, 6:511–519

15. Lagudah, E. S., Appels, R., Brown, A. H. D. and McNeil, D. (1991a). The molecular-genetic analysis of *Triticum tauschii*, the D-genome donor to hexaploid wheat. Genome, 34: 375–386.

16. Lagudah, E. S., Appels, R. and McNeil, D. (1991b). The Nor-D3 locus of *Triticum tauschii* natural variation and linkage to chromosome 5 markers. Genome, 34: 387–395.

17. Lagudah, E. S., Appels, R., McNeil, D. and Schachtman, D. P. (1993). Exploiting the diploid D genome chromatin for wheat improvement. In Gene conservation and exploitation. (J. P. Gustafson, R. Appels and R. Raven eds) Plenum Press, New York pp. 87–107.

18. Lander, E. S., Green, P., Abrahamson, J., Barlow, A., Daly, M. J., Lincoln, S. E. and Newburg, L. (1987). MAP-MAKER an interactive computer package for constructing primary genetic linkage maps of experimental and natural populations. Genomics, 1: 174–181.

19. Rivoal, R., Dosba, F., Jahier, J. and Pierre, J. S. (1986). Les lignees d'addition ble-*Aegilops ventricosa* Tausch. VI. Etude de la localisation chromosomique de la resistance a l'egard d'*Heterodera avenae*. Woll. Agronomic, 6: 143–148.

20. Sambrook, J., Fritsch, E. F., and Maniatis, T. (1989) Molcular Cloning, A Laboratory Manual. Cold Spring Harbor, N.Y.: Cold Spring Harbor Laboratory Press.

21. Sears, E. R. (1966). Nullisomic-tetrasomic combinations in hexaploid wheat. In Chromosome manipulations and plant genetics. (R. Riley and K. R. Lewis eds.) Oliver and Boyd, Edinburgh pp. 29–45.

22. Sharp, P. J., Chao, S., Desai, S. and Gale, M. D. (1989). The isolation, characterization and application in the Triticeae of a set of wheat RFLP probes identifying each homoeologous chromosome arm. Theor. Appl. Genet. 78: 342–348.

23. Slootmaker, L. A. J., Lange, W. and Schepers, J. (1974). Monosomic analysis of bread wheat of resistance to cereal root eelworm. Euphytica, 23: 497–503.

24. Smith, D. B. and Flavell, R. B. (1975). Characterisation of the wheat genome by renaturation kinetics. Chromosoma, 50: 223:242.

25. Weining, S. and Landridge, P. (1991). Identification and mapping of polymorphisms in cereals based on the polymerase chain reaction. Theor. Appl. Genet. 82: 209–216.

I claim:

1. An isolated nucleic acid molecule comprising a nucleotide sequence encoding a polypeptide which is capable of conferring, or enhancing resistance to a nematode in a plant, wherein said polypeptide comprises at least one amino acid sequence motif selected from the group consisting of p-Loop, kinase-2, or leucine-rich repeat motifs, which nucleic acid molecule is obtained by a method of:
    a) hybridizing genomic DNA, mRNA, or cDNA that comprises a nematode-resistance genetic sequence or a part or fragment thereof from said plant under low stringency conditions with one or more nucleic acid molecules that comprise at least 10 contiguous nucleotides in length from SEQ ID NO:1 or SEQ ID NO:3 for a period of time and under conditions sufficient to form a double-stranded nucleic acid molecule;
    b) detecting the hybridized nucleic acid molecules; and
    c) isolating said nucleic acid molecule comprising a nucleotide sequence encoding said polypeptide.

2. The isolated nucleic acid molecule according to claim 1, derived from a monocotyledonous plant selected from the group consisting of *Triticum tauschii*, wheat, maize, rice, oats, barley and rye and/or wild varieties and/or hybrids or derivatives and/or ancestral progenitors of same.

3. The isolated nucleic acid molecule according to claim 2 wherein said nucleic acid molecule comprises the nucleotide sequence set forth in SEQ ID NO:1 or SEQ ID NO:3, or a complementary nucleotide sequence thereto.

4. An isolated DNA molecule comprising a sequence of nucleotides which:
    (i) encodes or is complementary to a sequence encoding a polypeptide of plant origin which is capable of conferring, or enhancing nematode resistance in a plant; and
    (ii) comprises the nucleotide sequence set forth in SEQ ID NO: 1 or SEQ ID NO: 3 or a complementary nucleotide sequence thereto.

5. An isolated nucleic acid molecule which:
    (i) encodes or is complementary to a sequence encoding a polypeptide of plant origin which confers, or enhances nematode resistance in a plant; and
    (ii) hybridises under at least low stringency conditions to the nucleic acid molecule set forth in SEQ ID NO: 1 and/or SEQ ID NO: 3 or to a complementary strand thereof.

6. The isolated nucleic acid molecule according to claim 5 comprising the nucleotide sequence set forth in SEQ ID NO: 1 or SEQ ID NO:3.

7. A genetic construct comprising the nucleic acid molecule according to claim 5.

8. The genetic construct according to claim 7 wherein the nucleic acid molecule is operably linked to a promoter sequence.

9. The genetic construct according to claim 8 wherein the promoter sequence comprises nucleotides 1 to 1140 set forth in SEQ ID NO: 1, or a functional part thereof.

10. The genetic construct according to claim 7 capable of being expressed in a plant cell.

11. The genetic construct according to claim 10 wherein the plant cell is a monocotyledonous plant cell selected from the group consisting of *Triticum tauschlii*, wheat, maize, rice, oats, barley and rye and/or wild varieties and/or hybrids or derivatives and/or ancestral progenitors of same.

12. A genetic construct comprising an isolated promoter sequence which is derived from a cereal cyst nematode resistance gene wherein said promoter is capable of regulating the expression of a gene in a monocotyledonous plant cell and comprises nucleotides 1 to 1140 set forth in SEQ ID NO:1, or a functional part thereof.

13. An oligonucleotide molecule of at least 10 nucleotides in length capable of hybridising under low stringency conditions to the nucleotide sequence set forth in SEQ ID NO: 1 and/or SEQ ID NO:3 or to a complementary sequence thereto.

14. A nematode-resistant plant carrying the isolated nucleic acid molecule according to claim 5, wherein said plant is made nematode-resistant by virtue of the presence of said nucleic acid molecule in its genome and wherein said nucleic acid molecule has been introduced to the genome of said plant or the genome of a progenitor of said plant.

15. The nematode-resistant plant according to claim 14 wherein the nucleic acid molecule:
    (i) comprises all or part of the nucleotide sequence set forth in SEQ ID NO: 1 or SEQ ID NO:3; or
    (ii) hybridises under at least low stringency conditions to the nucleic acid molecule set forth in SEQ ID NO: 1 or SEQ ID NO:3 or to a complementary strand thereof.

16. The nematode-resistant plant according to claim 14 wherein the nucleic acid molecule is introduced into the plant by introgression.

17. The isolated nucleic acid molecule according to claim 1, derivable from a monocotyledonous plant selected from the group consisting of *Triticum tauschlii*, wheat, maize, rice, oats, barley and rye and/or wild varieties and/or hybrids or derivatives and/or ancestral progenitors of same.

18. The isolated nucleic acid molecule according to claim 1, wherein the nematode is a cereal cyst nematode.

19. The isolated nucleic acid molecule according to claim 18, derivable from a monocotyledonous plant selected from the group consisting of *Triticum tauschlii*, wheat, maize, rice, oats, barley and rye and/or wild varieties and/or hybrids or derivatives and/or ancestral progenitors of same.

20. The isolated nucleic acid molecule according to claim 3, wherein the nematode is a cereal cyst nematode.

21. The nematode-resistant plant according to claim 14, wherein said plant is a monocotyledonous plant selected from the group consisting of *Triticum tauschlii*, wheat, maize, rice, oats, barley and rye and/or wild varieties and/or hybrids or derivatives and/or ancestral progenitors of same.

22. The nematode-resistant plant according to claim 21, wherein the nematode is a cereal cyst nematode.

23. The nematode-resistant plant according to claim 14, wherein the nematode is a cereal cyst nematode.

24. The nematode-resistant plant according to claim 16, wherein said plant is a monocotyledonous plant selected from the group consisting of *Triticum tauschlii*, wheat, maize, rice, oats, barley and rye and/or wild varieties and/or hybrids or derivatives and/or ancestral progenitors of same.

25. The nematode-resistant plant according to claim 24, wherein the nematode is a cereal cyst nematode.

26. The nematode-resistant plant according to claim 16, wherein the nematode is a cereal cyst nematode.

27. The isolated nucleic acid molecule according to claim 1 wherein the step of detecting or isolating the hybridized nucleic acid molecule comprises amplifying the hybridized nucleic acid molecule in a polymerase chain reaction.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1614 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1138..1614

(xi) SEQUENCE DESCRIPTION: SEQ ID NO:1:

ATCCGGAGTC GTGGTTGTGG CCGCTGTCTT CCACTTGTGT ACGGTTTTCC CGTTGTCGAG    60

-continued

```
TGGCCTTCCT TCTTTCGGCC TTGCGGTTAA CAGGTTAGGG GCGCCGGTAG TGTTGTGGTG      120

TGTCATCTTT GGTGAGCTTA TTAATGTCGG CTTGTGGTGT CACATGGTGG TGGGTTCTCA      180

TTTAACGTCG AGGCGGTGAC CTCAGGTGGC GGTCCGTCAA GTCGGCTTCT CAACAAGCGT      240

CTTGGCGGCG GCCGTGGTGG CATTGTTTGG TCGTGTGGAC GGCGGAGGAT GCTAAGTTGG      300

GTGATCCTAG TGTCGGTGGT GCTTTGGCAC TGGCGGTGCC CAGATCGTGT TCTAGTGGTC      360

TGGCTTGGTA GTGACATGTT CACCTCGGTG TGGGCTGGTG CTCGGGAGGC CTAGTGTGGC      420

GTGGAAGAGT GCAACAAGGT CCGGCGATTT TCCTTGGAGC GAACTTTCAT CTTTGTTGGT      480

AGTTTAGGTA GCTTTGTGTT AGGGTGTGGT TCCTCCTATT TTCTTGTTTT TCTTTGATCT      540

GCTTTGTAAG AGGGTCTCCT CATCACCTTG TATCTCTTTG GTCGTGGTTC TTTATATATA      600

AAGCGGGGCC GAAGTAATTT TTGGTAGGAT TCACCAACAT CATGAGAACA AAGCACGAAA      660

ATATAGTAGT ACGGTAGTAG AGAATGTTAA TTCCTCTTGT ATCCAATGTT ATCTCTTGTA      720

TACCGTGATT CTTGCCCATC AGTATTCTCT TAGGCTTCTG TTAGCGAAAC AAAATTCCTT      780

CTTCCAAATT ACCAAACTTC TAGCTCATGA GTATGTTCAT ATAGTGCGCG GAGGATGTGC      840

GTGCCACATG CGTGCGCATG ATGGTGTTGA TAGACTAACA TGTGTGTGTG GTTTCTGTGT      900

GACTGCCTTG TGTTCTCTGC AAAACTAGGC TTTTGGCAAG TCAGTCTAGA TCCCTCGGCG      960

TATTTTTTAG AAGTATACCG GAGAGTAGAC GAATTCCCTA TATTACATTA GTCTTTTTTC     1020

TTTATTTAGT GTCATGATAG TTTATGTGAA GATAAAATCT CTCTTCTGTA ATGGTCACCT     1080

ATAATTTATT TTTTAAAGAT TTCTCTCTTG TTATTTGGGG TCTCGCAGGA GAGTGGC        1137

ATG TCA AAG AAA AAG TTG ATA GAC AGC CTG AAG AAG ATA GAA GAC AAT     1185
Met Ser Lys Lys Lys Leu Ile Asp Ser Leu Lys Lys Ile Glu Asp Asn
 1               5                  10                  15

ATA AAT GAA GCA CAC CAA ATT CTG GAT AAG CTT AAC TTG TCA AGC ATA     1233
Ile Asn Glu Ala His Gln Ile Leu Asp Lys Leu Asn Leu Ser Ser Ile
            20                  25                  30

AGT GAT GGA AAT AGA AGA CAT GTA ATG GAT GCT AAT CGT CCT ACT ACT     1281
Ser Asp Gly Asn Arg Arg His Val Met Asp Ala Asn Arg Pro Thr Thr
        35                  40                  45

GCA GTT TCT CCG CAT AAA GTA CTT GGT CGA GAT AAT GAG CGC GAC AAG     1329
Ala Val Ser Pro His Lys Val Leu Gly Arg Asp Asn Glu Arg Asp Lys
    50                  55                  60

ATC ATA AAA ATG CTT CAC AAA AAT GAA GGT GGT GTT CAA CCA AGC ACC     1377
Ile Ile Lys Met Leu His Lys Asn Glu Gly Gly Val Gln Pro Ser Thr
65                  70                  75                  80

AGC AAC AGT CTA TGC TTT TCT GTA ATT GGC ATA CAT GGA GTT GGT GGG     1425
Ser Asn Ser Leu Cys Phe Ser Val Ile Gly Ile His Gly Val Gly Gly
                85                  90                  95

TCA GGG AAA TCT ACC CTT GCA CAA TTG GTT TAT GCC CAT GAG GAA AAA     1473
Ser Gly Lys Ser Thr Leu Ala Gln Leu Val Tyr Ala His Glu Glu Lys
            100                 105                 110

GAC AAG AAA GAC AAC AAG GAA GGT CAC TTC GAC CTG GTT ATG TGG GTC     1521
Asp Lys Lys Asp Asn Lys Glu Gly His Phe Asp Leu Val Met Trp Val
        115                 120                 125

CAT GTC TCT CAG AAT TTT AGT GTG GGC GAC ATC TTC AAG GAG TTG TAT     1569
His Val Ser Gln Asn Phe Ser Val Gly Asp Ile Phe Lys Glu Leu Tyr
    130                 135                 140

GAG GCA GCT TCA GAG CCT AAG GTT CCA TGC CAT TCA ATA ACA TGA         1614
Glu Ala Ala Ser Glu Pro Lys Val Pro Cys His Ser Ile Thr
145                 150                 155
```

(2) INFORMATION FOR SEQ ID NO:2:

(i) SEQUENCE CHARACTERISTICS:
            (A) LENGTH: 158 amino acids
            (B) TYPE: amino acid
            (D) TOPOLOGY: linear (ii) MOLECULE TYPE: protein (xi) SEQUENCE DESCRIPTION: SEQ ID NO:2:

Met Ser Lys Lys Lys Leu Ile Asp Ser Leu Lys Lys Ile Glu Asp Asn
 1               5                  10                  15

Ile Asn Glu Ala His Gln Ile Leu Asp Lys Leu Asn Leu Ser Ser Ile
                20                  25                  30

Ser Asp Gly Asn Arg Arg His Val Met Asp Ala Asn Arg Pro Thr Thr
            35                  40                  45

Ala Val Ser Pro His Lys Val Leu Gly Arg Asp Asn Glu Arg Asp Lys
 50                  55                  60

Ile Ile Lys Met Leu His Lys Asn Glu Gly Gly Val Gln Pro Ser Thr
 65                  70                  75                  80

Ser Asn Ser Leu Cys Phe Ser Val Ile Gly Ile His Gly Val Gly Gly
                85                  90                  95

Ser Gly Lys Ser Thr Leu Ala Gln Leu Val Tyr Ala His Glu Glu Lys
               100                 105                 110

Asp Lys Lys Asp Asn Lys Glu Gly His Phe Asp Leu Val Met Trp Val
           115                 120                 125

His Val Ser Gln Asn Phe Ser Val Gly Asp Ile Phe Lys Glu Leu Tyr
       130                 135                 140

Glu Ala Ala Ser Glu Pro Lys Val Pro Cys His Ser Ile Thr
145                 150                 155

(2) INFORMATION FOR SEQ ID NO:3:

(i) SEQUENCE CHARACTERISTICS:
            (A) LENGTH: 1238 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..1238

(xi) SEQUENCE DESCRIPTION: SEQ ID NO:3:

GGT TCC ATG CCA TTC AAT AAC ATG AAT TCC TTG GGA AAA GAA TTG GAA        48
Gly Ser Met Pro Phe Asn Asn Met Asn Ser Leu Gly Lys Glu Leu Glu
 1               5                  10                  15

AGG AAA CTA GAT GGA AAG CGA TTC CTT CTG ATA CTG GAT GAT GTC TGG        96
Arg Lys Leu Asp Gly Lys Arg Phe Leu Leu Ile Leu Asp Asp Val Trp
                20                  25                  30

TGC AAT AAG GAT GTC AGC GAT CAG AAT CTA CCA GAG TTA CTT TCT CCA       144
Cys Asn Lys Asp Val Ser Asp Gln Asn Leu Pro Glu Leu Leu Ser Pro
            35                  40                  45

TTG AAG GTT GGA AAG AGA GGA AGC AAG ATC CTA GTG ACG ACT CGA AGT       192
Leu Lys Val Gly Lys Arg Gly Ser Lys Ile Leu Val Thr Thr Arg Ser
 50                  55                  60

AAA TAT GCA TTA CCG GTT CTA GGT CCT GGT GTG AGA TGT ACT GCC ATA       240
Lys Tyr Ala Leu Pro Val Leu Gly Pro Gly Val Arg Cys Thr Ala Ile
 65                  70                  75                  80

CCA GTA CCT GAG TTT GAT GAT ACC GCC TTC TTC GAG CTA TTC ATG CAC       288
Pro Val Pro Glu Phe Asp Asp Thr Ala Phe Phe Glu Leu Phe Met His
                85                  90                  95

```
TAT GCC CTG GAA GAA GGC CAA GAT CAG AGC CTG TTC TGT ATA ATT GGT      336
Tyr Ala Leu Glu Glu Gly Gln Asp Gln Ser Leu Phe Cys Ile Ile Gly
            100                 105                 110

GAG GAG ATA GCG AAA AAG CTG AAG GGG TCA CCT CTA GCT GCC AGA ACA      384
Glu Glu Ile Ala Lys Lys Leu Lys Gly Ser Pro Leu Ala Ala Arg Thr
        115                 120                 125

GTG GGA GGA AAT TTA CGT CGA CAA CCA GAT GTC GAC CAT TGG AGA AGA      432
Val Gly Gly Asn Leu Arg Arg Gln Pro Asp Val Asp His Trp Arg Arg
    130                 135                 140

GTC AGA GAT CAA GAC CTT TTC AAG GTA TGG GGA GGG CCT CTG TGG TGG      480
Val Arg Asp Gln Asp Leu Phe Lys Val Trp Gly Gly Pro Leu Trp Trp
145                 150                 155                 160

AGC TAC TAT CAG CTT GGT GAG CAG GCT AGG CGT TGC TTT GCT TAT TGC      528
Ser Tyr Tyr Gln Leu Gly Glu Gln Ala Arg Arg Cys Phe Ala Tyr Cys
                165                 170                 175

AGT ATT TTT CCT AGG AGA CAT CGC CTG TAC CGT GAT GAC CTA GTT AGA      576
Ser Ile Phe Pro Arg Arg His Arg Leu Tyr Arg Asp Asp Leu Val Arg
            180                 185                 190

CTT TGG GTT GCA GAA GGG TTC ATA AGA AGC ACA GAT GAA GGG GCG GAT      624
Leu Trp Val Ala Glu Gly Phe Ile Arg Ser Thr Asp Glu Gly Ala Asp
        195                 200                 205

ATT GAA GAT GTT GGT CAG GAA ATA TTT AAT GAA CTA TTG TCG ATC TCG      672
Ile Glu Asp Val Gly Gln Glu Ile Phe Asn Glu Leu Leu Ser Ile Ser
    210                 215                 220

TTT CTT CAA CCA GGA GGC ACG AAC AAC TCT TAT CTC GCC GGC ATT TAT      720
Phe Leu Gln Pro Gly Gly Thr Asn Asn Ser Tyr Leu Ala Gly Ile Tyr
225                 230                 235                 240

TAT GGC AAG GAA TAC TAT TTA GTT CAT GAT CTG CTG CAC GAT TTA GCA      768
Tyr Gly Lys Glu Tyr Tyr Leu Val His Asp Leu Leu His Asp Leu Ala
                245                 250                 255

GAG GCA GTA GCT GGC AGT GAC TGC TTC AGA ATT GAC AAT AAC GCG AGC      816
Glu Ala Val Ala Gly Ser Asp Cys Phe Arg Ile Asp Asn Asn Ala Ser
            260                 265                 270

CAG AAA GGA GGA GGA TGG ACA AGA GAT GTT CCC CGA GAC GTT CGG CAT      864
Gln Lys Gly Gly Gly Trp Thr Arg Asp Val Pro Arg Asp Val Arg His
        275                 280                 285

CTT TTT GTT CAG AGT TAT GAT GCA ACA TTG ATT ACT GAA AAG ATT CTT      912
Leu Phe Val Gln Ser Tyr Asp Ala Thr Leu Ile Thr Glu Lys Ile Leu
    290                 295                 300

GAA TTG AGA AAG TTA CAC ACT CTT ATC ATT TAT AGT GTT GGA GGG GAT      960
Glu Leu Arg Lys Leu His Thr Leu Ile Ile Tyr Ser Val Gly Gly Asp
305                 310                 315                 320

ACA CCA GTT GAG GAA ATA GTC ATC AAG AAC ATA CTC AAG AGT CTG CCA     1008
Thr Pro Val Glu Glu Ile Val Ile Lys Asn Ile Leu Lys Ser Leu Pro
                325                 330                 335

AAA CTG CGG GTA CTA GCA ATT GCT TCG AGT CTG GAG GAC AGT GCA TTT     1056
Lys Leu Arg Val Leu Ala Ile Ala Ser Ser Leu Glu Asp Ser Ala Phe
            340                 345                 350

ATT TGG AAA CCA GAT ACA TTC TCT GTC CCA GAA TCT GTT GGT CAA TTG     1104
Ile Trp Lys Pro Asp Thr Phe Ser Val Pro Glu Ser Val Gly Gln Leu
        355                 360                 365

AAA CAT CTG CGC TAT CTT GCT TTC CGG ACA GAT AGA GGA TGC CGA GTA     1152
Lys His Leu Arg Tyr Leu Ala Phe Arg Thr Asp Arg Gly Cys Arg Val
    370                 375                 380

ATT TTA CCA AGC AGT CTA AAC CAG CTT TAC CAG ATG CAA CTG CTA GAT     1200
Ile Leu Pro Ser Ser Leu Asn Gln Leu Tyr Gln Met Gln Leu Leu Asp
385                 390                 395                 400

TTT GGT CAA TGC CAT GAT TTG GTA TTT TGC TGT GAT GA                  1238
Phe Gly Gln Cys His Asp Leu Val Phe Cys Cys Asp
                405                 410
```

(2) INFORMATION FOR SEQ ID NO:4:

(i) SEQUENCE CHARACTERISTICS:
        (A) LENGTH: 412 amino acids
        (B) TYPE: amino acid
        (D) TOPOLOGY: linear (ii) MOLECULE TYPE: protein (xi) SEQUENCE DESCRIPTION: SEQ ID NO:4:

```
Gly Ser Met Pro Phe Asn Asn Met Asn Ser Leu Gly Lys Glu Leu Glu
 1               5                  10                  15

Arg Lys Leu Asp Gly Lys Arg Phe Leu Leu Ile Leu Asp Asp Val Trp
             20                  25                  30

Cys Asn Lys Asp Val Ser Asp Gln Asn Leu Pro Glu Leu Leu Ser Pro
         35                  40                  45

Leu Lys Val Gly Lys Arg Gly Ser Lys Ile Leu Val Thr Thr Arg Ser
     50                  55                  60

Lys Tyr Ala Leu Pro Val Leu Gly Pro Gly Val Arg Cys Thr Ala Ile
 65                  70                  75                  80

Pro Val Pro Glu Phe Asp Asp Thr Ala Phe Glu Leu Phe Met His
                 85                  90                  95

Tyr Ala Leu Glu Glu Gly Gln Asp Gln Ser Leu Phe Cys Ile Ile Gly
                100                 105                 110

Glu Glu Ile Ala Lys Lys Leu Lys Gly Ser Pro Leu Ala Ala Arg Thr
            115                 120                 125

Val Gly Gly Asn Leu Arg Arg Gln Pro Asp Val Asp His Trp Arg Arg
130                 135                 140

Val Arg Asp Gln Asp Leu Phe Lys Val Trp Gly Gly Pro Leu Trp Trp
145                 150                 155                 160

Ser Tyr Tyr Gln Leu Gly Glu Gln Ala Arg Arg Cys Phe Ala Tyr Cys
                165                 170                 175

Ser Ile Phe Pro Arg Arg His Arg Leu Tyr Arg Asp Asp Leu Val Arg
                180                 185                 190

Leu Trp Val Ala Glu Gly Phe Ile Arg Ser Thr Asp Glu Gly Ala Asp
            195                 200                 205

Ile Glu Asp Val Gly Gln Glu Ile Phe Asn Glu Leu Leu Ser Ile Ser
210                 215                 220

Phe Leu Gln Pro Gly Gly Thr Asn Asn Ser Tyr Leu Ala Gly Ile Tyr
225                 230                 235                 240

Tyr Gly Lys Glu Tyr Tyr Leu Val His Asp Leu Leu His Asp Leu Ala
                245                 250                 255

Glu Ala Val Ala Gly Ser Asp Cys Phe Arg Ile Asp Asn Asn Ala Ser
            260                 265                 270

Gln Lys Gly Gly Gly Trp Thr Arg Asp Val Pro Arg Asp Val Arg His
        275                 280                 285

Leu Phe Val Gln Ser Tyr Asp Ala Thr Leu Ile Thr Glu Lys Ile Leu
    290                 295                 300

Glu Leu Arg Lys Leu His Thr Leu Ile Ile Tyr Ser Val Gly Gly Asp
305                 310                 315                 320

Thr Pro Val Glu Glu Ile Val Ile Lys Asn Ile Leu Lys Ser Leu Pro
                325                 330                 335

Lys Leu Arg Val Leu Ala Ile Ala Ser Ser Leu Glu Asp Ser Ala Phe
            340                 345                 350

Ile Trp Lys Pro Asp Thr Phe Ser Val Pro Glu Ser Val Gly Gln Leu
        355                 360                 365
```

```
Lys His Leu Arg Tyr Leu Ala Phe Arg Thr Asp Arg Gly Cys Arg Val
    370             375             380

Ile Leu Pro Ser Ser Leu Asn Gln Leu Tyr Gln Met Gln Leu Leu Asp
385             390             395             400

Phe Gly Gln Cys His Asp Leu Val Phe Cys Cys Asp
                405             410
```